(12) United States Patent  
Krogh et al.

(10) Patent No.: US 7,579,587 B2  
(45) Date of Patent: Aug. 25, 2009

(54) THERMALLY ASSISTED MEMBRANE INTRODUCTION MASS SPECTROMETRY (MIMS) INTERFACE AND METHOD OF USE THEREOF

(75) Inventors: Erik Thomas Krogh, Nanaimo (CA); Christopher G. Gill, Nanaimo (CA)

(73) Assignee: Vancouver Island University, Nanaimo, British Columbia (CA)

( * ) Notice: Subject to any disclaimer, the term of this patent is extended or adjusted under 35 U.S.C. 154(b) by 268 days.

(21) Appl. No.: 11/621,451

(22) Filed: Jan. 9, 2007

(65) Prior Publication Data

US 2007/0181799 A1 Aug. 9, 2007

Related U.S. Application Data

(60) Provisional application No. 60/758,943, filed on Jan. 13, 2006.

(51) Int. Cl.  
*H01J 49/04* (2006.01)

(52) U.S. Cl. .................. 250/288; 250/281; 250/282

(58) Field of Classification Search ................ 250/281, 250/282, 288  
See application file for complete search history.

(56) References Cited

U.S. PATENT DOCUMENTS 5,448,062 A * 9/1995 Cooks et al. ............... 250/288  
5,517,026 A * 5/1996 Sickenberger et al. ...... 250/288

* cited by examiner

*Primary Examiner*—Jack I Berman  
(74) *Attorney, Agent, or Firm*—Klarquist Sparkman, LLP

(57) ABSTRACT

A membrane introduction mass spectrometry (MIMS) sampling interface is presented that demonstrates improved online performance for the direct, real-time measurement of semi-volatile organic compounds (SVOCs) in samples such as air and water, at parts-per-billion and parts-per-trillion levels. The device is based upon a capillary hollow fiber silicone (polydimethylsiloxane) membrane in a 'flow-over' configuration that is resistively heated on the membrane interior. One embodiment resistively heats using a coaxial nichrome wire, establishing a thermal gradient counter to the analyte concentration gradient. This arrangement allows for continuous and/or pulsed heating modes, affording excellent sensitivity for the online measurement of SVOCs while retaining sensitivity for volatile organic compounds (VOCs). In addition, the signal response time for SVOCs is reduced substantially over conventional MIMS methods. Separation and quantitation of analytes is achieved using quadrupole ion trap tandem mass spectrometry or selected ion monitoring mass spectrometry.

32 Claims, 7 Drawing Sheets

THERMALLY ASSISTED MEMBRANE INTRODUCTION MASS SPECTROMETRY (MIMS) INTERFACE AND METHOD OF USE THEREOF

CROSS REFERENCE TO RELATED APPLICATION

This application claims the benefit of U.S. Provisional Patent Application No. 60/758,943 filed Jan. 13, 2006, and entitled "Thermally Assisted Membrane Introduction Mass Spectrometry (MIMS) Interface And Method Of Use Thereof" which is hereby incorporated herein by reference.

FIELD

The present technology relates to a combination of a thermal element and a membrane for use in membrane introduction mass spectrometry. More specifically it relates to a heat element that establishes a thermal gradient that is opposite to the concentration gradient in a semi-permeable membrane and method of use for direct sample introduction in an on-line analytical method known as membrane introduction mass spectrometry.

BACKGROUND

The use of membrane introduction mass spectrometry (MIMS) as an online measurement strategy for volatile organic compounds (VOCs) and semi-volatile organic compounds (SVOCs) in air [1], water [2] and complex reaction media [3-7] has been well demonstrated over the past decade. The method provides continuous, direct introduction of sample to a mass spectrometric system without sample preparation or pretreatment steps and has been applied as a "real-time" monitoring strategy for dynamic chemical processes and environmental systems [3-10]. The theory and practice of MIMS is discussed in several recent reviews [11, 12]. The membrane sampling interface (typically a polydimethylsiloxane (PDMS) membrane) acts as a semi-selective barrier that rejects the bulk of the sample matrix, while allowing the permeation of VOC and SVOC analyte molecules across the membrane. Analytes are subsequently entrained by an inert sweep gas that is introduced directly into a mass spectrometer [13]. The principle advantages of membrane introduction are the ability to monitor selected analytes in complex matrices in an on-line system with temporal resolutions on the order of seconds to minutes. The sensitivity of MS detectors in general and the added selectivity afforded by tandem MS techniques makes MIMS a powerful analytical tool. MIMS is well suited for the analysis of non-polar, low molecular weight analytes, providing low detection limits (<ppb) and fast instrument response times (<1 min). However, the analysis of SVOCs by conventional MIMS provides unsatisfactory results characterized by slower response times and relatively high detection limits (when compared to VOCs).

The overall permeation of analyte across the membrane has been described as i) selective absorption into the membrane, ii) diffusion through the membrane itself and iii) desorption from the downstream membrane surface into the carrier gas [12, 13]. The permeation rate of analyte through the membrane and hence the response time of the measurement process is governed by physio-chemical properties of the permeating species and the concentration gradient across the membrane. In addition, both theory and experiment have shown the permeation rates are determined by properties of the membrane, including its composition, thickness, surface area and temperature. Several papers have appeared evaluating a variety of membrane geometries [3, 13-17] and membrane materials [14]. However, the greatest improvements in extending MIMS to less volatile molecules involve cryofocusing techniques [18] or some form of thermally assisted desorption, typically involving heating the entire MIMS interface assembly [19-21]. For example, Lauritsen [22] and Eberlin [23] have reported on methods in which sample is passed through the lumen of a hollow fibre membrane positioned in the EI mass spectrometer source. Heating the membrane by the EI filament led to greater analyte desorption and increased sensitivity. Soni et al. described the use of a low-power carbon dioxide laser to desorb analyte from a sheet membrane directly into a mass spectrometer source [24] and recently, Creaser et al. have developed a "universal MIMS interface" that incorporates heating and cooling to facilitate both VOC and SVOC measurements [25].

Thermal desorption methods have been successful in improving the analytical performance of MIMS to the analysis of SVOCs in air samples [25, 26]. By elevating the interface temperature after pre-loading the membrane with analyte, SVOCs permeate and desorb more rapidly. Thermal desorption methods for aqueous samples (in which both membrane and sample are heated) have been limited by much slower heating cycles and broadened desorption profiles, due to the relatively high heat capacity of water. This is further complicated by the increased permeability of the membrane to water vapour at increased temperatures. During the online analysis of SVOCs in aqueous samples the MIMS interface is typically heated to a maximum of 50-60° C. At higher temperatures, sufficient water vapour is transferred through the membrane to the mass spectrometer that the overall MS performance is degraded [27]. Furthermore, the partitioning of analyte into the PDMS membrane is less favored at elevated temperatures thus reducing the analytical sensitivity. These limitations can be circumvented by using a 'trap and release' approach in which the aqueous sample is exposed to the membrane and then removed, followed by a more rapid thermal desorption of (SVOC) analytes 'trapped' in the membrane [21]. However this approach comes at the expense of continuous (real-time) measurement capability. Riter et al. have demonstrated a 'single-sided MIMS' device which uses a double helical wire heater coil inside a membrane to desorb material from the inner surface of a membrane [28]. This device operates by exposing the sample to the same (inner) membrane surface that is ultimately exposed to a mass spectrometer (after a pump down cycle). Such methodology, although well suited for new membrane materials development research or as a pre-concentrator for fiber introduction mass spectrometry [29], does not facilitate 'real-time', temporally resolved measurements. In recent work by the Thomas group, an internally heated HFM-PDMS membrane is modeled and demonstrated as a means of effecting low resolution separations for ppm level VOC analytes using flame ionization detection [30]. Their work suggests that internally heated membrane capillaries can be used for the low resolution separation of analytes, and may prove useful for mixture analysis.

It is an object of the present technology to overcome the deficiencies in the prior art.

SUMMARY

SVOCs used to exemplify the present technology include 2-methoxyphenol (Guaiacol, GU), 2,4,6-trichloroanisole (TCA), biphenyl (BP), naphthalene (NA), Fluorene (FL), diethylphthalate (DEP) and 2-(perfluoroalkyl)ethanols (Fluorotelomer alcohol, FTA). These SVOCs have been chosen based on their environmental relevance. Guaiacol is representative of substituted phenols and is of interest as a potential woodsmoke marker in air samples [31]. TCA is a representative polyhalogenated aromatic of interest as a disinfection by-product in drinking water [32] and is responsible for cork taint in wines at pptr levels [33]. BP, NA and FL are representative polycyclic aromatic hydrocarbons. Diethylphthalates and fluorotelomer alcohols are common environmental and foodstuff contaminants. In general, the detection of these SVOCs by conventional MIMS is hampered by slow response times, low sensitivity and memory effects. Toluene (TOL) has been chosen as a representative VOC for comparison purposes.

One embodiment of the disclosed technology concerns a membrane interface arrangement for MIMS in which the sample flows over the outside of an internally heated hollow fibre membrane (HFM). This MIMS interface can be used for the direct, on-line measurement of SVOCs in a wide variety of complex samples, including both air and water, with several different operational modes, including 'trap and release' as well as continuous thermally assisted desorption. The logic behind the design is that a differential heating of the membrane is possible. The internal heater (in one embodiment, a co-axially arranged resistive wire passed through the centre of the HFM) preferentially heats the inner surface of the membrane that delivers analyte to the mass spectrometer. An internal heating strategy is employed to establish a thermal gradient that is opposite to the analyte concentration gradient across the membrane. This allows for continuous partitioning of analyte from the sample matrix into the HFM while simultaneously enhancing analyte transfer from the membrane to the mass spectrometer. The result is a dramatic increase in sensitivity and a marked decrease in response times for SVOCs compared to the conventional, external heating of a MIMS interface.

In one embodiment, a combination for real-time monitoring of volatile compounds and semi-volatile compounds is provided. The combination comprises:
   a hollow core membrane having an inner wall, an outer wall and a lumen;
   a heat element housed within the lumen;
   a power source in electrical communication with the heat element; and
   a mass spectrometer.

In one aspect, the heat element is a resistive wire.
In another aspect, the wire is a nichrome wire.
In another aspect, the wire is a 34 gauge wire.
In another aspect, the power source is a direct current power supply.
In another aspect, the power supply is adjustable.
In another embodiment, a method for on-line identification of analyte in a sample using membrane introduction mass spectrometry is provided. The method comprises:
   introducing a sample to a membrane;
   establishing a heat flux that is opposite to the mass flux across the membrane;
   desorbing the analyte from the membrane and into a stream of an inert gas; and
   introducing the analyte in the stream of the inert gas into the mass spectrometer for on-line analysis, thereby identifying an analyte.

In another aspect, the introduction of the sample is pulsed.
In another aspect, the introduction of the sample is continuous, direct introduction.
In another aspect, the sample is further defined as an aqueous sample.
In another aspect, the aqueous sample is a water sample.
In another aspect, the sample is further defined as a gaseous sample.
In another aspect, the sample is an air sample.
In another aspect, the desorption is defined as continuous desorption.
In another aspect, the desorption is further defined as pulsed desorption.
In another aspect, the inert gas is helium.
In another embodiment, a method for on-line identification and quantification of analyte in a sample using the combination defined above is provided. The method comprises:
   introducing a sample directly to the membrane;
   differentially heating the membrane;
   desorbing the analyte from the membrane and into a stream of an inert gas; and
   introducing the analyte in the stream of the inert gas into the mass spectrometer for analysis, thereby identifying and quantifying an analyte.

In one aspect, the analyte comprises volatile compounds or semi-volatile compounds or both volatile and semi-volatile compounds.

In another embodiment, a method for preparing a sample for on-line identification and quantification of analyte is provided. The method comprises:
   collecting the sample;
   introducing the sample directly to a semi-permeable membrane housed in the combination described above;
   establishing a temperature gradient that is opposite to a concentration gradient; and desorbing the analyte from the membrane into a stream of inert gas, thereby preparing a sample.

DEFINITIONS

Figure 1:
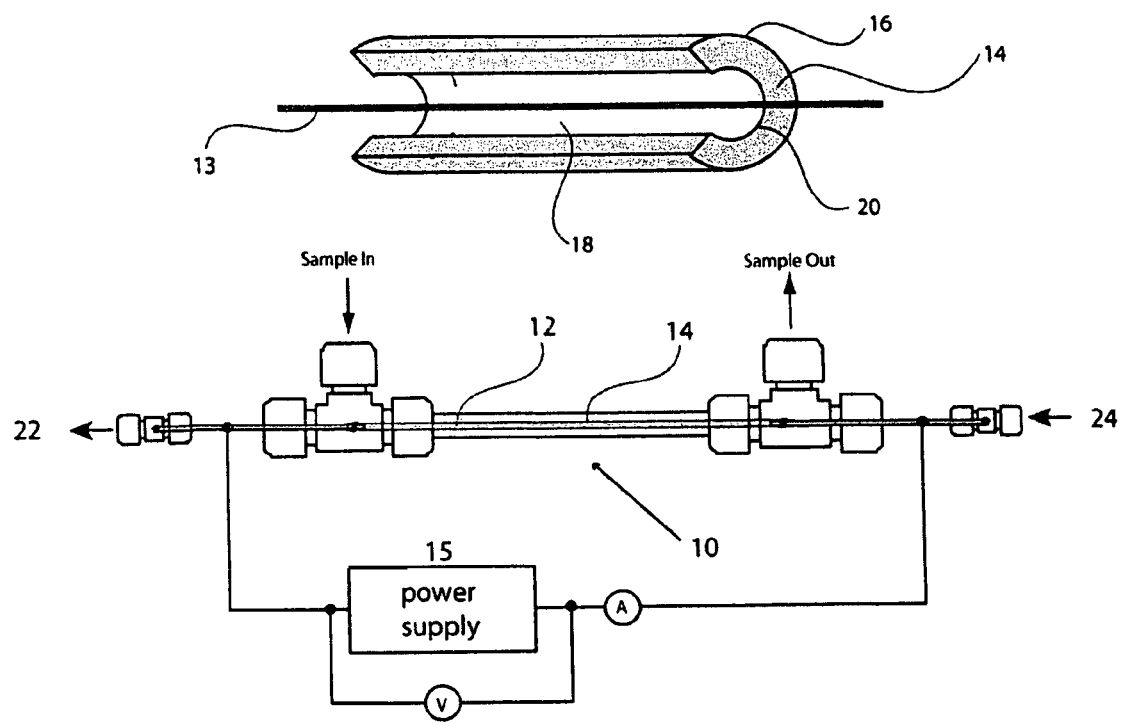
FIG. 1 is a plan view of an embodiment in accordance with the present technology, schematically illustrating an internally heated MIMS interface, with a resistive heating element coaxially mounted inside a PDMS hollow fibre membrane, and where electric contact is made with the heating element via attachment to hypodermic tubing.

On-line:
On-line measurements provide an analytical signal by passing the sample through a device without the need for subsequent sample handling. On-line measurements include real-time measurements.

Real-time:
Real-time measurements provide analytical signal from a device while the sample is being introduced in a continuous mode of operation. All real-time measurements are on-line, whereas not all on-line measurements provide real-time data.

Continuous Sample Introduction:
Continuous sample introduction is a mode of operation in which the sample flows over the membrane interface in an on-going fashion.

Pulsed Sample Introduction:
Pulsed sample introduction is a mode of operation in which the sample is flowed over the membrane interface for a set period of time.

Pulsed Thermal Desorption:
Pulsed thermal desorption is a mode of operation in which the sample is continuously flowed over the membrane interface and heating is turned on for a set period of time.

Heat Flux:
Heat flux refers to the net flow of heat across the membrane.

Temperature Gradient:
Temperature gradient refers to the variation of temperature from one side of the membrane to the other.

Mass Flux:
Mass flux refers to the net transport of chemical species across a semi-permeable membrane.

Concentration Gradient:
Concentration gradient refers to the variation in the concentration of a chemical species from one side of the membrane to the other.

Analyte:
Analyte refers to a particular molecule or group of molecular species of interest. Analytes include VOC, SVOC, organometalics, metal hydrides, metal carbonyls, main group fluoride compounds and other classes as outlined below in a non-exhaustive list of compounds with examples of specific compounds in each class.

Alkynes:
Examples of alkynes include, without limitation:
Acetylene
2-Pentyne,
1-Propyne,
Ethyl acetylene,
Propyl acetylene,
Butadienyl acetylene,
Vinyl acetylene Alcohols:
Examples of alcohols include, without limitation:
Ethanol
Butanol
Propanol
Hexanol
1-Octanol
2-(perfluorooctyl)ethanol
Fluorotelomer alcohols Alkaloids
Examples of alkaloids include, without limitation:
Caffeine
Tropine
Coniine
Nicotine Alkanes
    Examples of alkanes include, without limitation:
Isobutane
Isopentane
Neopentane
Methane
Ethane
Propane
n-Butane
n-Pentane
n-Hexane
n-Decane
n-Tetradecane
n-Pentadecane
n-Octadecane Alkenes:
    Examples of alkenes include, without limitation:
Ethene
Pentene
Bromo ethylene
Methyl Butene
Hexene
2-Methylpropene
2-methyl-1,3-butadiene
Trans 5-Pentadecene
1-Methyl Cyclohexene
Butadiene
Propene
4-Methyl-1-hexene
2-Ethyl-4-methyl-1-hexene
Cyclopentdiene
Cyclohexene
Cycloheptene
Cyclooctene
1-Methyl-1-cyclopentene
Methylene cyclohexene Amines:
    Examples of amines include, without limitation:
Aniline
Ammonia
Butylamine
Ethyl-amine
Dimethyl Amine
Trimethyl Amine
Triethanol Amine Aromatic Aldehydes:
    Examples of aromatic aldehydes include, without limitation:
Benzaldehyde
Vanillin
Cinnamaldehyde Aromatic Ketones:
    Examples of aromatic ketones include, without limitation:
Acetophenone
Bezophenone
Benzoquinone
1,4-napthhoquinone Aromatics:
    Examples of aromatics include, without limitation:
Benzo-fluoranthene
Benzyl alcohol
Benzene
Toluene
Ethyl benzene Biogenic Plant Volatiles:
    Examples of aromatics include, without limitation:
Acetaldehyde
Isoprene
Trans 2-hexenal
1-butanol
2-ethyl-1-hexanol
nonanal
benzaldehyde
tetramethylthiourea
2-methylfuran
trans-3-hexenol
trans-3-hexenyl acetate Biphenyls:
    Examples of biphenyls include, without limitation:
Polychlorinated Biphenyls
Polybrominated Biphenyls
Tetrabromo-diphenylether
Pentabromo-diphenylether Breath Volatiles:
    Examples of breath volatiles include, without limitation:
Acetone
Hexanal
Pentane
Carbonyl sulfide
Carbon disulfide
Hydrogen Sulphide,
Methyl Mercaptan
Dimethyl Sulphide Chlorofluorocarbons:
    Examples of chlorofluorocarbons include, without limitation:
Di-Chloro di-Fluoroethane
Tri-Chloro-Fluoroethane
Bromo-Chloro di-Fluoromethane
Freons Cycloalkanes:
    Examples of cycloalkanes include, without limitation:
Cyclopropane
Cyclobutane
Cyclopentane
Cyclohexane
Cycloheptane
Isopropyl cyclopropane
1,3-Dimethyl Cyclopentane Cycloalkyl Halide:
    Examples of cycloalkyl halides include, without limitation:
Dichlorocyclopropane
Chlorocyclohexane
2-Chloro 1-1-isopropylcyclopropane Disinfection By-products:
    Examples of disinfection by-products include, without limitation:
Chloroform
Trihalomethane
Dichloromethane
Dichloroacetonitrile
Cyanogenchloride Epoxides:
  Examples of epoxides include, without limitation:
Methylepoxypropane
Deildrin
Chloropropyleneoxide Esters:
  Examples of esters include, without limitation:
2-Propen-1-yl hexanoate
Pentyl ethanoate
Pentyl hexanoate
Benzyl ethanoate
2-Methylpropyl ethanoate
Ethyl hexanoate
Ethyl 3-phenyl-2-propenoate
Ethyl methanoate
Ethyl 3-methylbutanoate
Ethyl heptanoate
Ethyl 2-hydroxypropanoate
Ethyl nonanoate
3,7-Dimethyl-2,6-octadien-3-yl ethanoate
3,7-Dimethyl-2,6-octadien-3-yl pentanoate
5-Methyl-2-(1-methylethyl)cyclohexanol ethanoate
Methyl 3-phenyl-2-propenoate
Methylphenyl ethanoate
Methyl 2-hydroxybenzoate
Methyl 2-aminobenzoate
Diethylphthalate Ethers:
  Examples of esters include, without limitation:
Dimethyl ether
Ethyl isopropyl ether
Methyl-n-butyl ether
Di-n-pentyl ether
Di-isobutyl ether
Methyl t-butyl ether
Di-n butyl ether
Di-isobutyl ether
Dipropylene glycol methyl ether
Tripropylene glycol monomethyl ether
Triclosan Ethylene Oxide:
  Examples of ethylene oxide include, without limitation:
Ethylene oxide
Cis-1,2-Dimethylethylene oxide Flavoring Agent:
  Examples of flavoring agents include, without limitation:
Isoamyl acetate
Ethyl propionate
d-limonene
Ethyl-(E,Z)-2,4-decadi eon ate
Allyl hexanoate
Methyl salicylate
Iodomethane Fragrance Compounds:
  Examples of fragrance compounds include, without limitation:
Octanol
1-Phenyl ethanone
Camphor
Iodomethane
Menthol Gasoline Additives:
  Examples of gasoline additives include, without limitation:
2-Methyl-2-butene
Manganese pentacarbonyl
Methyl tertiary butyl ether
Tetraethyl lead
Ethanol Gasoline Components:
  Examples of gasoline components include, without limitation:
Isooctane
Cyclohexane
Acetylene
Benzene
Toluene
Naphthalene Halogenated Alkenes:
  Examples of halogenated alkenes include, without limitation:
Trans-1,2-Dichloroethene
2-methyl-3-chloropropene
Trichloroethylene
1-Trifluoromethyl-3-chlorobenzene
1,3-dibromo-3-chloropropane Halogenated Esters:
  Examples of halogenated esters include, without limitation:
Methyl 3-chloro-4-methoxybenzoate
2,4-Dichlorobutyl ethanoate Hydrazines:
  Examples of hydrazines include, without limitation:
1,2-diphenylhydrazine
Hydrazine
Methyl hydrazine Hydrochlorofluoro Compounds:
  Examples of hydrochlorofluoro compounds include, without limitation:
Dichlorofluorethane
Pentafluorodichloropropane
1,1-Dichloro-1-fluoroethane
2-Chloro-1,1,1,2-tetrafluoroethane Isocyanates:
  Examples of isocyanates, without limitation:
Toluene diisocyanate
Methyl isocyanate Isothiocyanates:
  Examples of isothiocyanates include, without limitation:
Allyl isothiocyanate
Butenyl isothiocyanate
p-Hydroxybenzyl isothiocyanate
Benzyl-isothiocyanate Ketones:
  Examples of ketones include, without limitation:
Acetone
Acetoacetate
Acetophenone
2-Butanone Mercaptans:
  Examples of mercaptans include, without limitation:
Methyl mercaptan
Ethyl mercaptan
2-Butene-1-thiol Metal Carbonyls:
  Examples of metal carbonyls include, without limitation:
Chromium carbonyl Iron pentacarbonyl
Manganese hexacarbonyl
Tungsten carbonyl Metal Hydrides:
    Examples of metal hydrides include, without limitation:
Arsenic hydride
Selenium hydride
Lead hydride
Boron hydride Metallocenes:
    Examples of metallocenes include, without limitation:
Ferrocene Metalloids:
    Examples of metalloids include, without limitation:
Organoarsenides
Dimethylmercury
Tetraethyllead Nitriles:
    Examples of nitrites include, without limitation:
Ethanenitrile
Cyclobutanenitrile
Pentanedinitrile
Acetonitrile.
Acrylnitrile
Acetonitrile.
Isobutyronitrile.
m-Tolunitrile.
n-Valeronitrile .
Nitrophthalonitrile
p-Tolunitrile
Phthalonitrile
Propionitrile NitroAlkanes:
    Examples of nitroalkanes include, without limitation:
Nitromethane
Nitroethane
Nitropropane
Nitrobutane Nitroaromatics:
    Examples of nitroaromatics include, without limitation:
Nitrobenzene
2,4-Dinitrotoluene
2-Nitroaniline
2,4,6-Trinitrotoluene Organometallics:
    Examples of organometallics include, without limitation:
Ferrocene
Diethylmercury
Trimethylarsenic
Molybdenum hexacarbonyl
Tetraethyl lead Perfluorocarbons:
    Examples of perfluorocarbons include, without limitation:
Perfluoromethylcyclohexane
Perfluorooctanoic acid Phenols
    Examples of phenols include, without limitation:
4-Chloro-3-methylphenol
2-Chlorophenol
2,4-Dimethylphenol
4,6-Dinitro-2-methylphenol
2,4-Dinitrophenol
2,6-Dichlorophenol
4-Methylphenol (p-Cresol)
2-Nitrophenol
4-Nitrophenol
Pentachlorophenol
2,3,4,6-Tetrachlorophenol
2,4,5-Trichlorophenol
2,4,6-Trichlorophenol Phenylisocyanate:
    Examples of phenylisocyanates include, without limitation:
Methylphenylisocyanate
4,4-Diphenylmethane diisocyanate Pheromones:
    Examples of pheromones include, without limitation:
(3S, 6R)-3-Methyl-6-isopropenyl-9-decen-1-yl acetate
(3S, 6S)-3-Methyl-6-isopropenyl-9-decen-1-yl acetate
(1R-Z)-1-Methyl-2-(1-methylethenyl)cyclobutane ethanol
(Z)-2-(3,3-Dimethylcyclohexylidene)ethanol
(E)-(3,3-Dimethylcyclohexylidene)acetaldehyde
(Z)-(3,3-Dimethylcyclohexylidene)acetaldehyde Polyhalogenated Alkanes:
    Examples of polyhalogenated alkanes include, without limitation:
1,1,2-Trichlorotrifluoroethane
1,2-Dichlorohexafluorocyclobutane
1,1-Dichloroethane
1,1,2-Trichloroethane
1,1,1-Trichloroethane Polyhalogenated Alkenes:
    Examples of polyhalogenated alkenes include, without limitation:
Trichloroethylene
Hexachlorobutadiene
Hexachlorocyclopentadiene
Tetrachloroethylene Polyhalogenated Alkynes:
    Examples of polyhalogenated alkynes include, without limitation:
Dichloroethyne
Bromochloroethyne
3-Bromo-3-chloropropyne
3-Bromo-3,3-dichloropropyne Reduced Sulfur Compounds:
    Examples of reduced sulfur compounds include, without limitation:
Hydrogen sulfide
Carbonyl sulfide
Carbon disulfide
Dimethyl disulfide Silyl Compounds:
    Examples of silyl compounds include, without limitation:
Tetramethylsiloxane
Bis-(trimethylsilyl)trifluoroacetamide
N-Methyltrimrthylsilyltrifluoroacetamide
Allyldimethylchlorosilane
Bis-(diethylamino)dimethylsilane Sulfides:
    Examples of sulfides include, without limitation:
Dimethylsulfide
Carbondisulfide
Dimethyldisulfide
Methanethiol Sulfonamides
   Examples of sulfonamides include, without limitation:
Sulfacetamide
Sulfabenzamide
Sulphanilamide Sulfones:
   Examples of sulfones include, without limitation:
Dimethyl Sulfone
Chlorophenylmethyl Sulfone
Chloromethyl Sulfone Sulfoxide:
   Examples of sulfoxides include, without limitation:
4-Chlorophenylmethyl Sulfoxide
Dimethyl Sulfoxide
Ethyl Methyl Sulfoxide Terpenes:
   Examples of terpenes include, without limitation:
Limonene
Pinene
Piperene
Camphene
Cymene
Farnesene
Caryophyllene Terpenoids:
   Examples of terpenoids include, without limitation:
Linalool
Limonene
Myrcene
Cineole
Pinene
Ocimene Thiols
   Examples of thiols include, without limitation:
Benzenethiol
1,2-Dimercaptoethane
3,3-Dimethylbutanethiol
1-Hexadecanethiol
1,6-Hexanedithiol
Ethanethiol
Cyclopentanethiol
2-Butanethiol
1-Butanethiol
2-Mercaptomethylpyrazine
2-Mercaptoethanol
4-Mercapto-4-methyl-2-pentanone
3-Mercapto-2-butanol
3-((Mercapto-1-methylpropyl)thio)2-butanol
2,3-Butanedithiol Thioethers
   Examples of thioethers include, without limitation:
Dimethyl sulfide
1-methylthiopropane
Diphenyl sulfide VOC:
   Volatile compounds are molecules characterized by a relatively high vapour pressure, typically >1,000 Pa.

SVOC:
   Semi-volatile compounds are molecules with vapor pressures in the range of about 0.1 to about 1,000 Pa.

DETAILED DESCRIPTION

A thermally assisted membrane introduction mass spectrometry (MIMS) interface, generally referred to as 10 is shown in FIG. 1. The MIMS interface is a combination of a coaxial heater 12 and a hollow fiber membrane (HFM) 14 The design permits differential heating of the membrane 14. In use, a sample, which is continuously flowing over the outer wall 16 of the membrane 14, introduces analyte to the membrane 14 and also continuously cools the outer wall 16 of the membrane 14. The coaxial heater 12 is a resistive heating wire 13 and a direct current power source 15. The resistive heating wire 13 generically referred to as a heat element, is housed in the lumen 18 defined by the cylindrical inner wall 20 of the capillary HFM 14. In use, the coaxial heater 12 preferentially heats the inner wall 20 of the membrane 14 exposed to the mass spectrometer 22. The resultant heating establishes a temperature gradient that is counter to the concentration gradient which increases the mass flux for SVOCs across the membrane. It also allows for continuous partitioning of analyte from the sample into the membrane 14 with enhanced permeation from the membrane 14 into a helium stream 24 that is passed to the mass spectrometer 22. This results in both increased sensitivity and decreased response times for SVOCs over that possible with heating of the entire MIMS interface. The following describes embodiments of the present technology and applications for the direct, online measurement of SVOCs in both air and water using several different operational modes. Performance comparisons between a conventionally heated interface and embodiments of the interface of the present technology also are presented.

EXAMPLE

The experiments for this work were performed using a quadrupole ion trap mass spectrometer with an external ion source (Polaris-Q™, Thermo-Electron, San-Jose, Calif., USA) equipped with an in-house constructed MIMS interface. To monitor the analytes of interest for this work, full scan, selected ion monitoring (SIM) and tandem mass spectrometry (MS/MS) were employed. In most cases, the analytical signals from MS/MS experiments are presented. Physical data and specific mass scan parameters are given in Table 1.

The MIMS interface used here was constructed in-house by modifying a previously described interface design [17]. Briefly, the unmodified MIMS instrument consists of a hollow fibre, polydimethylsiloxane membrane (a working embodiment dimensions were 10.0 cm, 0.94 mm OD, 0.51 mm ID, 0.22 mm thickness, 0.050 $cm^3$ total volume, 3.0 $cm^2$ outside surface area, Silastic® brand, Dow Corning, Midland, Mich., USA). The membrane was mounted in a flow through casing constructed of 0.25" Swagelok™ (Supelco, Bellefonte, Pa., USA) connectors and stainless steel tubing. A low flow of helium sweep gas (UHP grade, 99.999% pure, 2.7 mL/min) is passed through the inside of the membrane. The exit helium flow is subsequently directed through a metal jet separator (model MJSC/HP5890, 15 mL/min jets, SGE, Austin, Tex., USA) and then to the mass spectrometer (200° C. ion source, base pressure $1.0 \times 10^{-5}$ Torr) via a heated transfer line (150° C.). The jet separator was backed ($5.5 \times 10^{-2}$ Torr) using a mechanical roughing pump (Pascal 2005SD, Alcatel, Paris, France) equipped with an inline molecular sieve trap (4 inch diameter, 13 Å sieve pore size, KJ Lesker Inc, Pittsburgh, Pa., USA). To facilitate a variety of comparison experiments, the MIMS interface was mounted entirely inside a programmable gas chromatograph oven (Trace GC™, Thermo-Electron, San-Jose, Calif., USA). This GC was used to control overall MIMS temperature as well as regulation of the helium sweep gas flow.

The details of the modifications made to the MIMS interface are summarized in FIG. 1. A nickel-chromium resistive heating wire (34 gauge, Parr Instrument Co., Moline, Ill., USA) was coaxially passed through the center of the hollow capillary fibre membrane. Electrical contact with this wire was made via two sections of stainless steel hypodermic tubing (22 gauge, Vita Needle Co., Needham, Mass., USA) attached to either end of the membrane (used also to position the membrane in the interface described above). An adjustable, direct current power supply (model LX20-3, Xantrex Technology Inc., Vancouver BC, Canada) was connected to each side of the MIMS interface and thus the heater wire (see FIG. 1). Both voltage and current were monitored during these experiments using digital multi-meters (Mastercraft Inc., Houston Tex., USA).

For this work, Guaiacol and toluene gas standards were prepared using a dynacalibrator™ (Model 450, VICI Metronics, Poulsbo, Wash., USA) equipped with gravimetrically calibrated permeation tubes (Guaiacol, 32 ng/min @ 50° C., Toluene, 22.6 ng/min @ 50° C.) and UHP grade air (99.999% pure). These were subsequently transferred from the dynacalibratorTM to the MIMS interface via a short length of 0.25" OD Teflon™ tubing (Cole-Parmer, Vernon Hills, Ill., USA). All aqueous standards were prepared with ACS grade chemical reagents, including 2-methoxyphenol, 2,4,6-trichloroanisole, biphenyl, fluorene, toluene, diethylphthalate and Zonyl® BA-L (a 2-(perfluoroalkyl)ethanol containing a mixture of C7/C8 perfluoroalkyl groups) (Sigma Aldrich, Oakville, Ont., Canada) and naphthalene (Fisher Scientific, Nepean, Ont., Canada). All aqueous standards were prepared with high purity deionized (DI) water (Model MQ Synthesis A10, Millipore Corp., Billerica, Mass., USA). Aqueous samples were circulated through the MIMS interface using a peristaltic pump (Model 77200-62 Masterflex Easy-Load II with LS-25 viton pump tubing, Cole-Parmer Ltd, Concord, Ont., Canada) at a flow rate of 220 mL/min. To eliminate any potential memory effects between runs, the interface was heated to 120° C. while flushing with UHP grade air. For aqueous experiments, the interface was subsequently flushed at 30° C. with DI water.

RESULTS AND DISCUSSION

A. Parameter Optimization

To assess the viability and characteristics of disclosed embodiments of the present technology, a number of parametric studies were conducted on the internally heated HFM interface. From this work (described in detail below), the upper power limit for sustained internal heating of the membrane was found to be about 1.86 W (0.52 A, 3.58 V) for air samples and about 12.4 W (1.40 A, 8.85 V) for aqueous samples. These limits were chosen because higher power settings resulted in the appearance of characteristic PDMS fragmentation peaks (e.g. m/z=207, 209, 281), indicating some degree of membrane degradation consistent with the observations of others working with heated PDMS membranes [21]. The substantially greater power possible with aqueous samples is attributed to the enhanced cooling of the outer membrane surface provided by the continuous flow of aqueous sample.

Figures 2A, 2B:
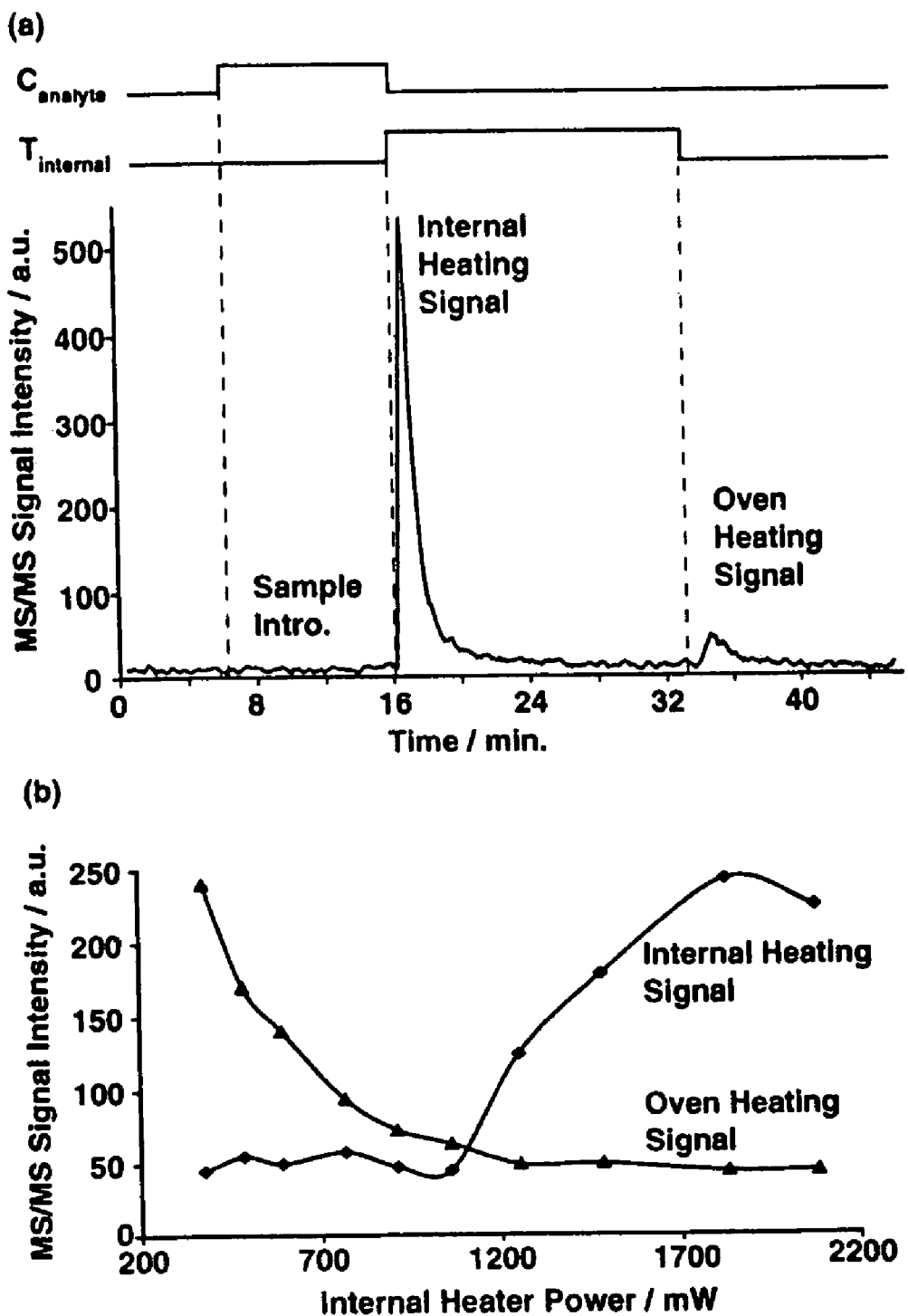
FIG. 2(a) shows signal intensity using the embodiment of FIG. 1 for one semi-volatile organic compound, guaiacol (2-methoxyphenol) in air samples, and provides a sample MS/MS analytical signal for the pulsed desorption of SVOC analyte in air using the internal resistive heating element. A 6.52 ppbv GU sample was introduced for a 10 minute interval at 30° C., followed by thermal desorption by internal heating. After thermal desorption, a ballistic heating cycle to 120° C. was initiated to remove analyte retained by the interface.
FIG. 2(b) shows optimization data for the embodiment of FIG. 1 for one semi-volatile organic compound, guaiacol (2-methoxyphenol) in air samples, and illustrates a parametric study of the operational characteristics for the internally heated membrane interface obtained for the analysis of 2.65 ppbv GU in air sample. Following the method outlined in FIG. 2(a), the MS/MS signal intensities for GU at various powers applied to the internal heater are given, as are the signals resulting from a post-run heating using the GC oven.

A representative analytical run generated for an air sample containing 6.5 parts per billion by volume (ppbv) Guaiacol using a 'trap and release' mode is depicted in FIG. 2(a). In order to evaluate desorption profiles and residual SVOC in the membrane, a series of experiments were performed in which analyte was loaded on the exterior of the membrane, thermally desorbed using an internal heating wire and then oven heated to 'bake-off' any residual analyte. After purging the sampling line with UHP air, a Guaiacol-spiked air sample was introduced for a set time interval to load the membrane (the sampling lines were then returned to UHP air until the end of the run). At this point, the interior of the membrane was resistively heated at powers ranging from about 200 to about 2,000 mW. Internal heating at supplied powers in the upper part of this range were accompanied by a strong analytical signal for Guaiacol. Each experiment was followed by a bake-off cycle, in which the heater wire was switched off and the entire membrane was ballistically heated to 120° C. and held for 10-15 minutes in a GC oven (until any residual Guaiacol signal was eliminated). This was done in part to monitor the amount of residual analyte retained by the interface following the internal heater wire desorption, as well as to eliminate (potential) memory effects in subsequent measurements.

The results of a systematic investigation of internal wire heating are presented in FIG. 2(b). This figure illustrates that heating powers below 1000 mW showed no or little improvement in the MS/MS signal intensity for Guaiacol. At powers greater than 1000 mW, the MS/MS signal intensity varied directly with heater power up to about 2000 mW. The intensity of the Guaiacol signal during "bake-off" decreases as the internal heating power increased from 200 to 1000 mW, indicating that large amounts of SVOC remain in the membrane after internal heating at lower applied power. This is consistent with the poor sensitivity and long fall times characteristic for SVOCs by conventional MIMS techniques conducted at lower temperatures. When the heating wire was powered above 1000 mW, much less SVOC remains in the membrane, leading to a markedly improved desorption efficiency that results in greater analytical sensitivity and minimal memory effects. Based upon this study, an upper internal heating power of 1.86 W for air samples was selected and used for all subsequent work. Similar experiments conducted using aqueous samples showed that optimum performance occurred at 12.4 W internal heating power.

Response times for disclosed experiments as characterized as follows. In 'trap and release' mode, in which a heating pulse results in the mass transfer of a pre-loaded 'plug' of analyte, response times are measured as the full width at half maximum intensity (FWHM) of the desorption profile. The duty cycle time is measured sample-to-sample and includes sample loading, thermal desorption and cooling. For continuous sampling real-time analysis in which there is a constant supply of analyte, the analytical signal rises to a maximum value as the system establishes a steady state mass transfer. In such situations, 10 to 90% rise and fall times are reported.

B. Trap and Release Mode in Air Samples

Figure 3:
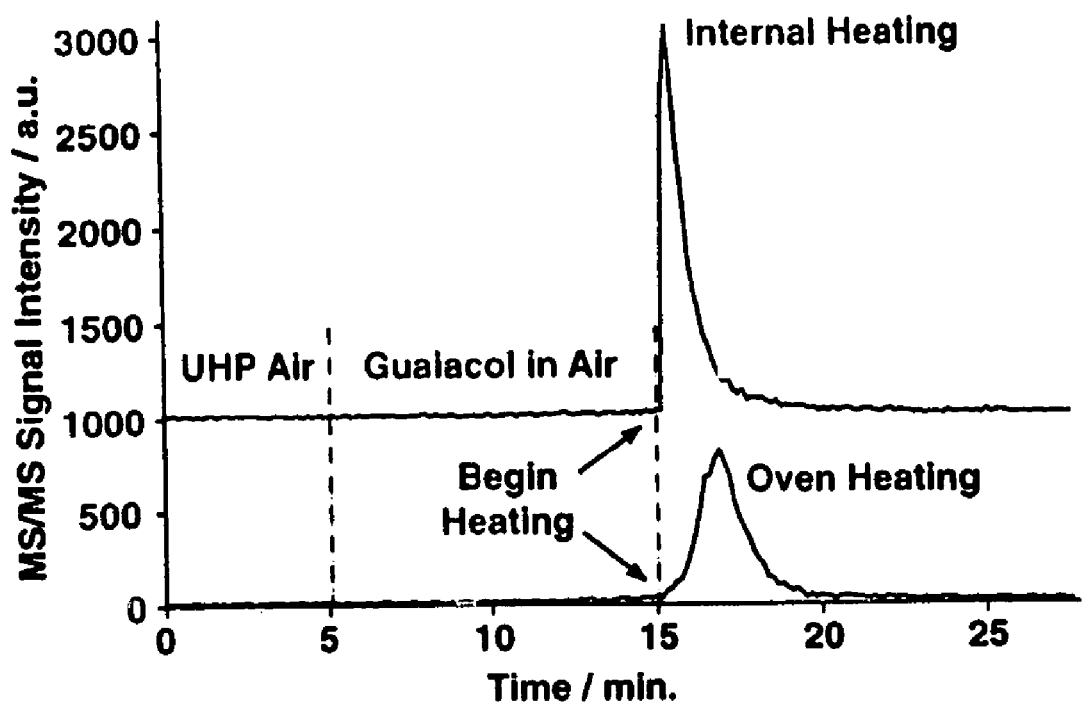
FIG. 3 illustrates thermal desorption of guaiacol in air using the embodiment of FIG. 1 and an oven of the prior art to compare internal resistive heating versus external oven heating for SVOC in air using a 'trap and release' sampling mode. After achieving a stable baseline using UHP air, a 24.6 ppbv GU sample was passed over the membrane interface for 10 minutes, followed by a UHP air for the duration of the run. Internal heating results in the immediate desorption of GU from the membrane (intensity=~2000 a.u., rise time=15 seconds FWHM=30 seconds). Ballistic heating of the GC oven to 120° C., resulted in the delayed appearance of the FU desorption peak (intensity=~800 a.u., rise time=70 seconds, FWHM=78 seconds).

The ability to internally heat the membrane results in a faster analytical response than that observed using external heating strategies. FIG. 3 compares the analytical signals obtained for a 24.6 ppbv Guaiacol air standard (10 minute membrane loading cycle) followed by internal versus external membrane heating. Differences in the thermal desorption peak profiles are attributed to the fact that the internal wire heats the membrane selectively and far more rapidly than is possible via external heating. The greater desorption peak intensity and narrower peak widths associated with internal heating are analytically advantageous resulting in greater sensitivity and shorter cycle times. Guaiacol is a typical SVOC that is difficult to analyze by MIMS without some form of thermal assistance (extremely long instrument response times with poor sensitivity at ambient temperatures). The detection limit (DL) for Guaiacol in air in the absence of thermal assistance (membrane isothermal at 30° C.) is typically >1 ppbv with a long rise time ($\geq$20 minutes) [31]. Using the GC oven to externally heat the membrane in a thermal desorption cycle (ballistic heating to 120° C.) or the internal resistive heating strategy improves the calculated DLs to about 20 pptrv (Table 2). However, thermal desorption via internal heating results in a narrower desorption profile of 36 sec (FWHM) as compared to a FWHM of 78 sec using the GC oven. In the studies presented above for the analysis of SVOCs in air samples, the analytical performance of the internally heated membrane interface is similar or slightly improved oven an externally membrane heating.

C. Continuous Sampling Mode in Air

The analysis of SVOCs in air samples in continuous sampling mode with the internal heater continuously powered at 1.8 W resulted in a reduction in analytical sensitivity. This is consistent with earlier observations for air samples analyzed using externally heated MIMS interfaces and can be attributed to a reduced solubility of the analyte in PDMS at higher temperatures [12, 13]. Because there is little cooling of the membrane exterior (due to the relatively low heat capacity of the flowing air sample), the temperature of the entire membrane is elevated during these experiments.

D. Trap and Release Mode in Water Samples

Figures 4A, 4B:
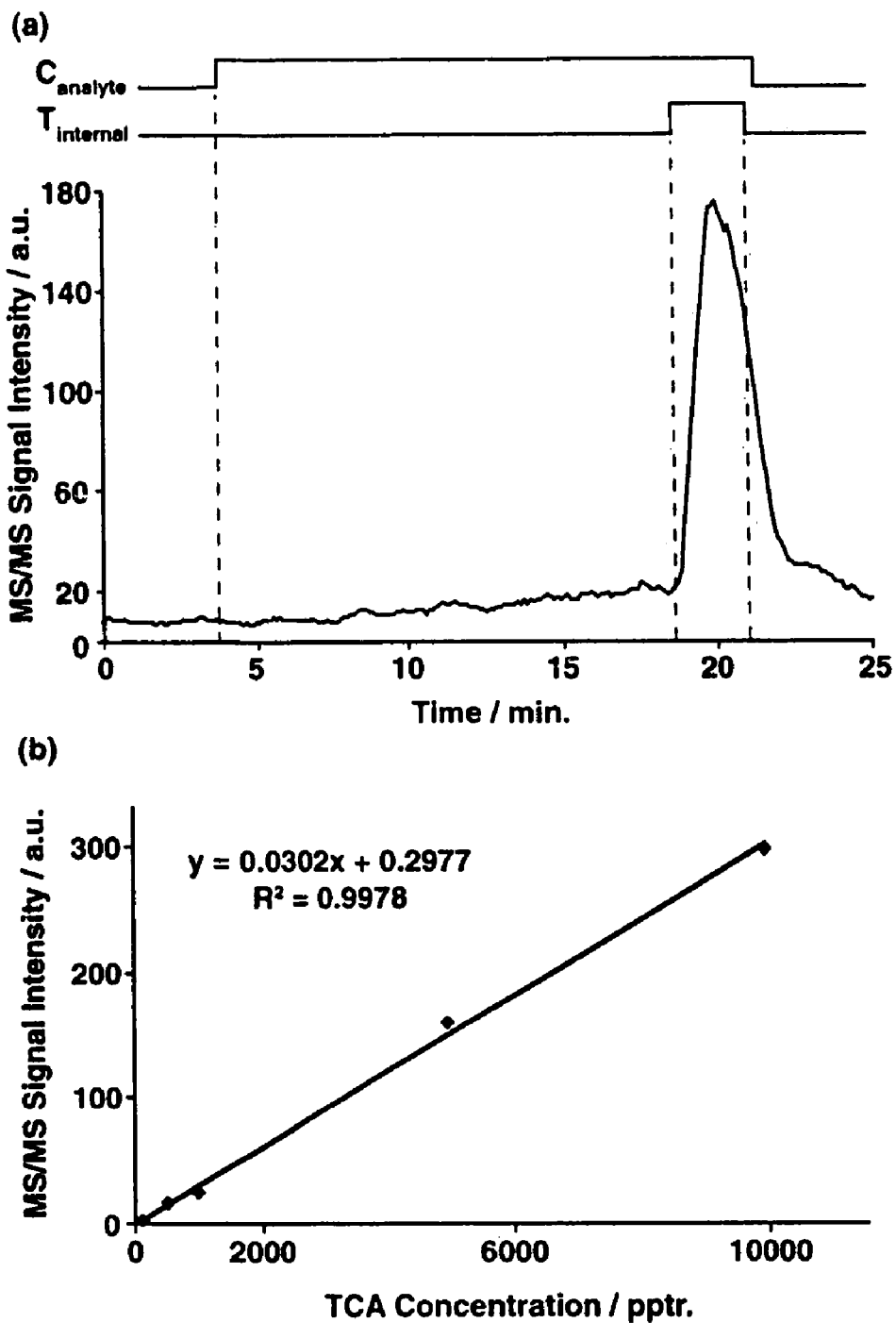
FIG. 4(a) shows signal intensity for trichloroanisole (TCA) in water using the embodiment of FIG. 1, and provides a representative MS/MS analytical signal for an 5 ppb aqueous TCA solution using 'trap and release' mode. Sample was loaded for 15 minutes at 30° C. followed by desorption with internal heating. The aqueous sample flowed over the HFM during internal heating cycle. No analytical signal was observed when the internal heater was off.
FIG. 4(b) is a linear calibration curve for aqueous TCA standards (100-10,000 pptr) obtained in the manner described for FIG. 4(a). The baseline subtracted MS/MS desorption peak intensities are plotted against concentration.

A similar thermal desorption approach was applied to the detection of SVOCs in aqueous samples. The sample was typically flowed over the HFM for 10 minutes (increased sampling times yield increased sensitivity), followed by a rapid desorb cycle using internal heating. In contrast to the 'trap and release' mode used in air, it should be noted that the aqueous sample is continuously flowed over the exterior of the membrane during the heating cycle (depicted in FIG. 4(*a*)). This modification has several advantages, including cooling the outer membrane surface and maintaining a high permselectivity for SVOC analytes. Furthermore, since only the inner membrane surface is being heated, we eliminate the need for a drying cycle (used by others prior to applying the desorption pulse) thus reducing the duty cycle time. In this operational mode, we observe a dramatic increase in sensitivity for SVOCs in aqueous samples (Table 2). This new technique allows for the rapid screening and quantitation of SVOC analytes at concentrations previously undetectable by conventional or externally heated MIMS. FIG. 4(*b*) is a calibration curve for aqueous 2,4,6-trichloroanisole (TCA) standards obtained using pulsed internal heating of the membrane. This calibration data suggests that satisfactory linear analytical response for aqueous TCA can be obtained in the parts per billion to parts per trillion (ppb-pptr) range. Similar results have been obtained for a mixture of C7/C8 fluorotelomer alcohols.

Figure 5:
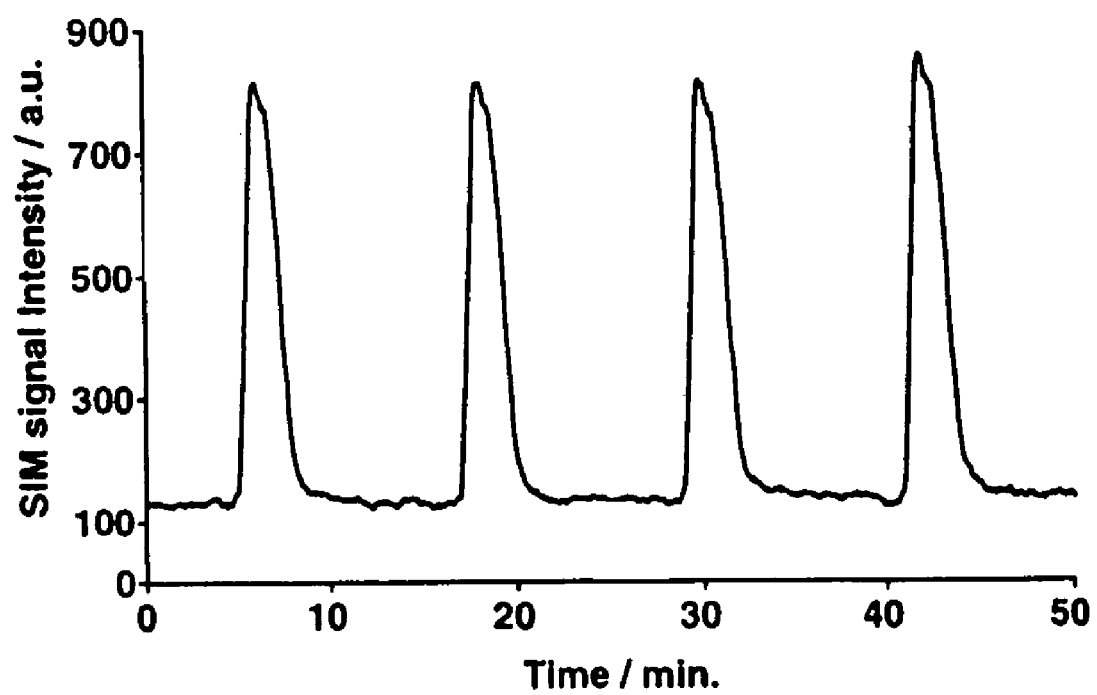
FIG. 5 shows signal intensity for biphenyl in water using the embodiment of FIG. 1 for the repetitive internal heating of an aqueous SVOC sample. For this data, a 1 L aqueous BP solution (98 pptr) re-circulated through the membrane interface at 30° C. to reach steady state permeation. The membrane was then internally heated in 2 minute pulses at 10 minute intervals. The mean rise and fall times are 44 and 65 seconds, respectively. The relative standard deviation between desorption peak heights was 1.3%.

FIG. 5 depicts the selected ion monitoring (SIM) signal for a 98 pptr aqueous solution of biphenyl (BP) in response to repeated internal heating pulses applied after the BP permeation had reached a steady state at ambient temperature. Internal heating enhanced the BP analytical signal dramatically and demonstrated excellent signal reproducibility (1.3% RSD). The rise and fall times for BP in response to internal heating are 44 and 65 secs, respectively.

E. Continuous Sampling Mode in Water

Figures 6A, 6B:
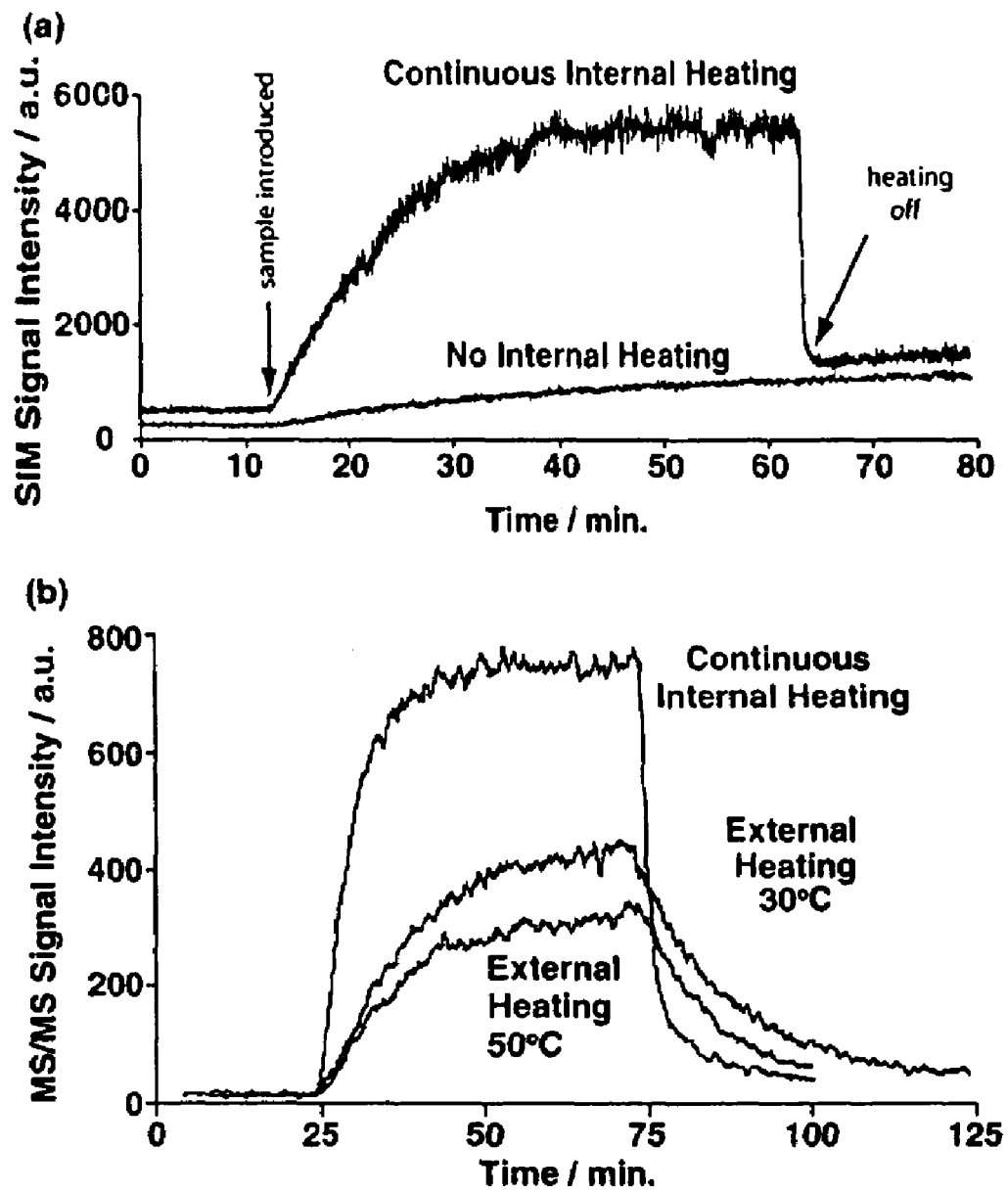
FIG. 6(a) compares the signal intensity and response time obtained with no heating of the prior art to heating using an embodiment of the present technology for a 1.6 ppb aqueous NA solution (re-circulated from a 1 L reservoir) using continuous internal heating (rise time=19.4 minutes) versus no internal heating (rise time>63 minutes). In each case, sample was maintained at 30° C. Note: traces are offset by 125 intensity units for clarity.
FIG. 6(b) compares the signal intensity and response time obtained with heating of the prior art to heating using an embodiment of the present technology for aqueous GU using continuous internal heating versus external membrane heating (isothermal GC oven). At 30° C. a 1 ppm GU sample yielded a signal intensity of ~400 a.u. with a rise time of 22.4 minutes. At 50° C., the same concentration gave a reduced signal intensity of ~300 a.u. with a rise time of 32.5 minutes. With continuous internal heating, a 500 ppb GU sample resulted in an observed signal of 800 a.u. and a rise time of 11.8 minutes. In all cases, the sample was recirculated through the interface from a 1 L reservoir maintained at 30° C.

The previously described 'trap and release' mode for aqueous samples affords improved sensitivity for SVOC molecules, but loses some of the 'real-time' capabilities of a direct sampling interface such as MIMS. To this end, a continuous monitoring mode of operation was evaluated using the internally heated interface with aqueous samples. FIG. 6(*a*) illustrates the analytical signals (SIM) for an aqueous 1.6 ppb naphthalene (NA) solution with no internal heating and using continuous desorption at 12.4 W. This figure shows both an approximately ten-fold increase in the observed signal intensity and a concomitant decrease in signal rise time for continuous internal membrane heating. Similar results were observed for all of the SVOC molecules examined. Continuous desorption mode has been operated for extended periods of time ($\geq$300 minutes) without any degradation in analytical performance.

In contrast, externally heated MIMS interfaces (e.g. using a GC oven to heat the entire MIMS interface) have limited operational temperatures (<60° C) in continuous monitoring mode for aqueous samples. The data presented in FIG. 6(*b*) further illustrates the advantages of continuous internal heating for SVOC analysis in aqueous solution. Aqueous samples of Guaiacol (GU) were introduced to the MIMS interface held isothermally at both 30° C. and 50° C. The observed decrease in signal intensity at higher sample temperatures is consistent with other researchers and attributed to the increased permeation of water across the membrane [27]. This is further supported by the higher base pressures observed for the jet separator backing pumps during aqueous sample introduction at elevated sample and membrane interface temperatures. For comparison, FIG. 6(*b*) also presents the analysis of a 500 ppb aqueous GU solution (half the concentration used above) obtained using continuous internal heating. A four-fold increase was observed in sensitivity for GU using continuous internal heating versus 30° C. isothermal. In addition, the rise time decreased from 22.4 mins at 30° C. to 11.8 mins with internal heating. This further demonstrates that continuous internal membrane heating outperforms external heating strategies for SVOC measurement in aqueous solutions.

Figure 7:
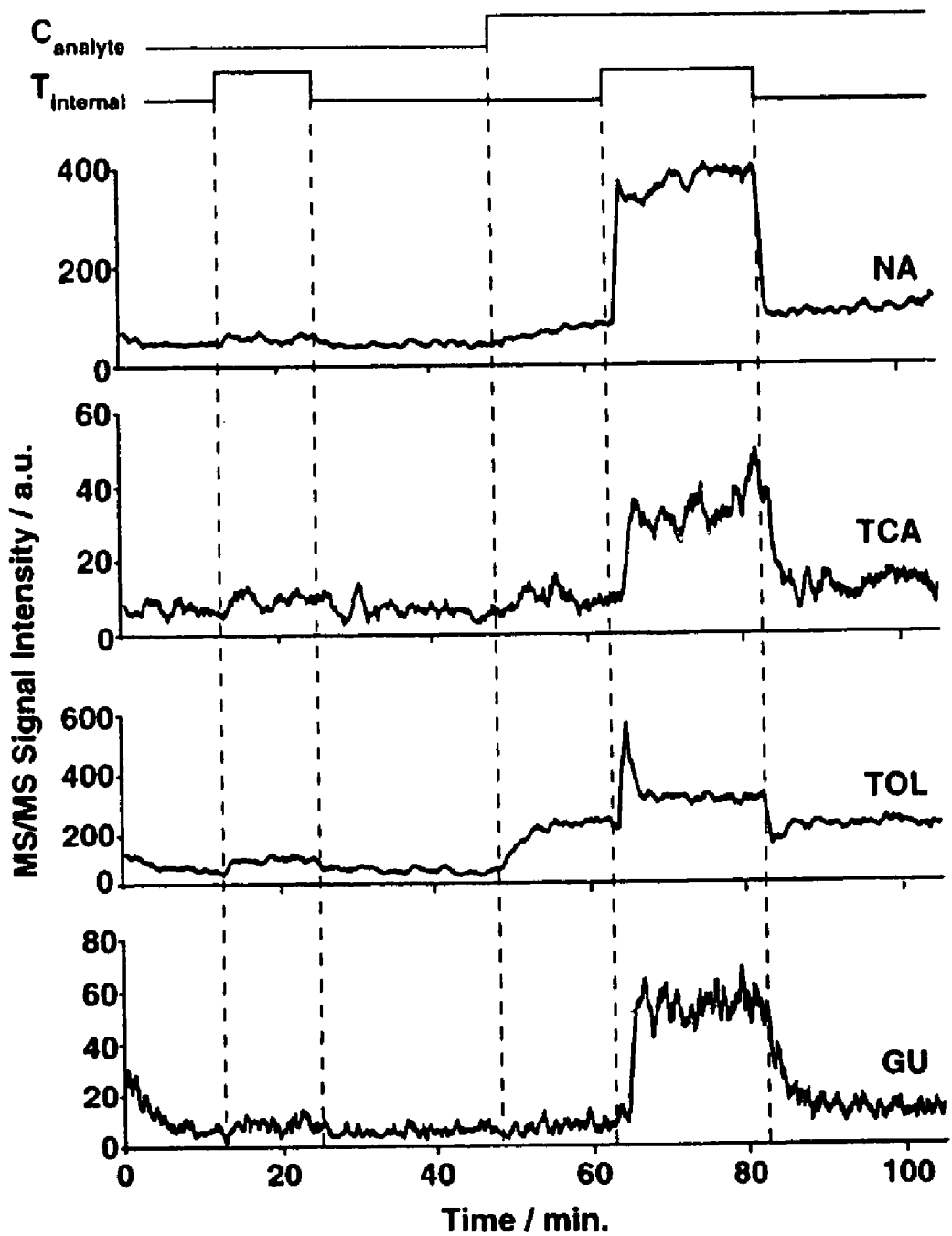
FIG. 7 shows analytical signals obtained for an aqueous mixture of VOC and SVOC's using internally heated membrane interface. Baseline was established by re-circulating deionized water in 1 L reservoir maintained at 30° C. An internal heating cycle was initiated to monitor the heating blank. After a stable baseline was re-established, a combined standard solution was injected. The concentrations are 670 pptr NA, 890 pptr TCA, 340 pptr TOL and 50 ppb GU. After internal heating stops, the baseline returns to pre-internal heating levels for all analytes.

As a final demonstration of the capabilities of continuous sampling mode for the internally heated MIMS interface, an aqueous mixture containing NA (670 pptr), TCA (890 pptr), GU (50 ppb) and TOL (340 pptr) was analyzed. The data presented in FIG. 7 illustrate sensitivity improvements in the continuous internal heating mode for three SVOCs and one VOC at concentrations approaching their detection limits. When the sample is introduced at ambient temperature (no internal heating), the TOL signal quickly rises to a steady state, whereas the signals for SVOCs rise very slowly (NA and TCA) or not at all (GU). Activating the internal heater results in an immediate and appreciable signal increase for all compounds in the mixture with rise times ranging from 54 to 76 secs for the SVOCs examined. Similar results have been obtained when GU, NA, TCA, and a C7/C8 FTA were spiked into a natural river water sample. When internal heating is discontinued, the analytical signals for SVOCs are dramatically reduced to ambient steady state levels (fall times similar to rise times). Detection limits based upon this data are given in Table 2.

F. Comparison of Measured Detection Limits

A comparison of detection limits (based on S/N=3) for SVOCs in both air and water appears in Table 2. Internal thermally assisted desorption improves sensitivity markedly for analytes in aqueous solution with the 'trap and release' mode providing the greatest sensitivity for the SVOCs examined. The DLs for aqueous samples in the continuous sampling mode are improved roughly one order of magnitude (4-10×) lower using internal heating element relative runs at 30° C. This improved sensitivity is accompanied by a faster rise time resulting in greater applicability for real-time analysis. Although estimated DLs for continuous sampling mode at 30° C. are included for comparison purposes, it should be noted that rise times at this temperature are greater than 60 minutes, making isothermal measurement at 30° C. impractically slow for most analytical applications. Further sensitivity enhancements (4-25×) are attained using the internal heating element in a 'trap and release' mode of operation.

For the analysis of SVOCs in air, continuous internal heating provided no significant improvements over external heating modes. Sensitivity improvements were observed for SVOCs in air samples in 'trap and release' modes. Guaiacol, which was not detectable at 600 pptrv using continuous heating strategies, was easily detected when it was loaded on the membrane followed by thermally assisted desorption. Although, the internal heating approach resulted in marginally higher DLs, it should be noted that internal heating yielded faster response times and shorter duty cycle times as noted in FIG. 3.

We believe that there are several reasons for the improved detection limits reported in this work. Common to all operational modes are the inherent sensitivity of ion trap (due to ion accumulation for trace analytes prior to their ejection/detection) and the use of an in-line jet separator to enrich analyte in the He sweep gas stream and a slightly thicker PDMS HFM (wall thickness=220 μm) than used by others (typically 170 μm). Given the dimensions of our PDMS membrane, the total volume is roughly 0.050 cm$^3$. Other workers have reported HFM with 0.64 mm OD, 0.30 mm ID [21, 34]. Although these thinner membranes are inherently faster to respond to a concentration gradient, the total volume of PDMS, (which limits the mass of analyte loaded) is 0.025 cm$^3$ for 10 cm length (roughly 50% relative to our system). The internal heating approach results in significant sensitivity enhancements, by establishing a temperature gradient that preferentially desorbs analyte into the interior of the hollow fibre membrane. This results is a greater mass transfer from the outside of the membrane into the lumen interior and ultimately to the MS detector.

The foregoing is a description of an embodiment of the technology. As would be known to one skilled in the art, variations that do not alter the scope of the technology would be contemplated. For example, the heat element could be a material other than the nichrome wire described above and the casing and connectors could be constructed of non-conducting polymer, for example, but not limited to Teflon™ or other inert polymers. Similarly, the hypodermic tubing could be replaced by deactivated silica capillary, for example, but not limited to. The foregoing facilitates the use of the interface in high ionic strength samples where electrolysis may be an issue. Also, the membrane can be any membrane that is used in MIMS that can be differentially heated. It would be also known to one skilled in the art, that the method of the technology could be applied to the study of a wide range of samples, containing a wide range of semi-volatile organic compounds and volatile organic compounds and that the studies described above are only exemplary. Samples could be, for example, but not limited to, blood, urine, food extracts, drinking fluids, water sources, effluent, industrial fluids, including samples of high ionic strength, and various extracts. The apparatus can also be applied to selected ion monitoring mass spectrometry. When the wire is not heated, the interface retains all of the properties of a conventional MIMS apparatus.

TABLE 1

Physical data[34], SIM Ions and MS/MS transitions monitored for the target molecules examined by this work.

| Compound | B.P./° C. | P°/Pa† | SIM m/z/Th | MS/MS Transition/Th |
|---|---|---|---|---|
| Biphenyl | 246 | 6.9 | 153, 154 | |
| Fluorene | 295 | 0.79 | 165, 166 | |
| Napthalene | 218 | 38 | 102, 128 | 128 → 102 |
| Guaiacol | 204–206 | 14 | 124 | 124 → 81, 109 |
| Toluene | 110.6 | 3786 | 91, 92 | 91 → 65 |
| 2,4,6-Trichloroanisole[35] | 260 | 1.4 | 210 | 210 → 167, 168, 195, 196 |
| Diethylphthalate | 298 | 0.84 | 149 | 149 → 93, 105, 121 |
| C7/C8 2-(perfluoroalkyl) ethanol | 145–245 | NA | 127 | 127 → 77 |

†Vapour pressures at 25° C. (reported as sub-cooled liquid values for solids).

TABLE 2

Detection limit comparison for the target analytes examined by this work using the various operational modes presented.

Detection Limits$^a$ (DL) for Aqueous Samples/pptr

| Target Analyte | Measured Concn. | Isothermal 30° C. Continuous Sampling Mode | Internal Heating Continuous Sampling Mode | Measured Concn. | Internal Heating Trap and Release Mode$^c$ |
|---|---|---|---|---|---|
| Guaiacol | 50000 | ND | 5200 | 5600 | 1300 |
| Fluorene | 45000 | (140)$^b$ | (15) | 89 | 10 |
| Biphenyl | 50000 | (65) | (8) | 98 | 3 |
| Trichloroanisole | 890 | (840) | 200 | 100 | 4 |
| Naphthalene | 670 | (110) | 26 | 82 | 4 |
| Toluene | 340 | 50 | 37 | 340 | 18 |

Detection Limits$^a$ (DL) for Air Samples/pptrv

| Target Analyte | Measured Concn. | Isothermal 30° C. Continuous Sampling Mode | Isothermal 60° C. Continuous Sampling Mode | External Heating Trap and Release Mode$^d$ | Internal Heating Trap and Release Mode |
|---|---|---|---|---|---|
| Guaiacol | 600 | ND | ND | 14 | 24 |
| Toluene | 580 | 280 | 320 | 91 | 140 |

$^a$All DL are based upon S/N = 3
$^b$Numbers in parentheses denote DL for signals with rise times ≧60 minutes and are included for comparison purposes only (not analytically useful).
$^c$Obtained for five challenges (as in FIG. 5).
$^d$Desorption via ballistic external heating to 120° C.

REFERENCES

The following references are incorporated herein by reference in their entirety.

1. Cisper, M. E.; Gill, C. G.; Townsend, L. E.; Hemberger, P. H. Anal. Chem. 1995; 67: 1413.
2. Soni, M.; Bauer, S.; Amy, J. W.; Wong, P.; Cooks, R. G. Anal. Chem. 1995; 67: 1409.
3. Nelson, J. H. L.; Krogh, E. T.; Gill, C. G.; Friesen, D. A. J Environ. Sci. Health, Part A. 2004; 39: 2307. DOI: 10.1081/LESA-200026269

4. LaPack, M. A., Tou, J. C., Enke, C. G. Anal. Chem. 1991; 63: 1631.
5. Creaser, C. S.; Santos, L. F.; Lamarca, D. G.; New, A.; Wolff, J. C. Anal. Chim. Acta. 2002; 454: 137. DOI: 10.1016/S0003-2670(01)01514-8
6. Johnson, R. C.; Cooks, R. G.; Srinivasan, N.; Schell, D. Rapid Commun. Mass Spectrom. 1997; 11: 363. DOI: 10.1002/(SICI)1097-0231(19970228)11:4<363::AID-RCM857>3.0.CO;2-Z
7. Pedersen, E. J.; Urbansky, E. T.; Marinas, B. J.; Margerum, D. W. Environ. Sci. Technol. 1999; 33: 4239. DOI: 10.1021/es990153q
8. Short, R. T.; Fries, D. P.; Kerr, M. L.; Byrne, R. H. J. Am. Soc. Mass Spectrom. 2001; 12: 676. DOI: 10.1016/S1044-0305(01)00246-X
9. Fries, D. P.; Short, R. T.; Langebrake, L. L.; Patten, J. T.; Kerr, M. L.; Kibelka, G.; Burwell, D. C.; Jalbert, J. C. Field Anal. Chem. Technol. 2001; 5: 121. DOI: 10.1002/fact.1013
10. Virkki, V. T.; Ketola, R. A.; Ojala, M.; Kotiaho, T.; V., K.; Grove, A.; Facchetti, S. Anal. Chem. 1995; 67: 1421.
11. Ketola, R. A.; Kotiaho, T.; Cisper, M. E.; Allen, T. M. J. Mass Spectrom. 2002; 37: 457.
12. Johnson, R. C.; Cooks, R. G.; Allen, T. M.; Cisper, M. E.; Hemberger, P. H. Mass Spectrom. Rev. 2000; 19: 1.
13. LaPack, M. A.; Tou, J. C.; Enke, C. G. Anal. Chem. 1990; 62: 1265.
14. Maden, A. J.; Hayward, M. J. Anal. Chem. 1996; 68: 1805. DOI: 10.1021/ac9509216.
15. Westover, L. B.; Tou, J. C.; Mark, J. H. Anal. Chem. 1974; 46: 568.
16. Brodbelt, J. S.; Cooks, R. G. Anal. Chem. 1985; 57: 1153.
17. Slivon, L. E.; Bauer, M. R.; Ho, J. S.; Budde, W. L. Anal. Chem. 1991; 63: 1335.
18. Bocchini, P.; Pozzi, R.; Andalo, C.; Galletti, G. C. Anal. Chem. 2001; 73: 3824. DOI: 10.1021/ac010249e
19. Riter, L.; Takats, Z.; Charles, L.; Cooks, R. G. Rapid Commun. Mass Spectrom. 2001; 15: 1520. DOI: 10.1002/rcm.401
20. Riter, L. S.; Takats, Z.; Cooks, R. G. Analyst. 2001; 126: 1980. DOI: 10.1039/b105857f
21. Creaser, C. S.; Weston, D. J. Anal. Chem. 2000; 72: 2730. DOI: 10.1021/ac9914768.
22. Lauritsen, F. R.; Ketola, R. A. Anal. Chem. 1997; 69: 4917. DOI: 10.1021/ac970570q
23. Mendes, M. A.; Eberlin, M. N. Analyst. 2000; 125: 21. DOI: 10.1039/a908654d
24. Soni, M. H.; Callahan, J. H.; McElvany, S. W. Anal. Chem. 1998; 70: 3103. DOI: 10.1021/ac9804361.
25. Creaser, C. S.; Lamarca, D. G.; dos Santos, L. M.; New, A. P.; James, P. A. Analyst. 2003; 128: 1150. DOI: 10.1039/b305085h
26. Allen, T. M.; Cisper, M. E.; Hemberger, P. H.; Wilkerson, C. W., Jr. Int. J. Mass Spectrom. 2001; 212: 197. DOI: 10.1016/s1387-3806(01)00487-0
27. Wong, P. S. H.; Cooks, R. G. Anal. Chim. Acta. 1995; 310: 387. DOI: 10.1016/0003-2670(95)00143-N
28. Cotte-Rodriguez, I.; Handberg, E.; Noll, R. J.; Kilgour, D. P. A.; Cooks, R. G. Analyst. 2005; 130: 679. DOI: 10.1039/b417791f
29. Rezgui, N. D.; Kanu, A. B.; Waters, K. E.; Grant, B. M. B.; Reader, A. J.; Thomas, C. L. P. Analyst. 2005; 130: 755. DOI: 10.1089/b414005b
30. Thompson, A. J.; Nelson, J. H. L.; Creba, A. S.; Freisen, D. A.; Krogh, E. T.; Dills, R. L.; Simpson, C. D.; Gill, C. G., Proc. 52nd Am. Soc. for Mass Spectrom. Conf., Nashville, Tenn., June, 2004.
31. Karlsson, S.; Kaugare, S.; Grimvall, A.; Boren, H.; Savenhed, R. Water Sci. Technol. 1995; 31: 99. DOI: 10.1016/0273-1223(95)00462-V
32. Waterhouse, A. L.; Ebeler, S. E., *Chemistry of Wine Flavor*. Oxford University Press: New York, 1999.
33. Riter, L. S.; Charles, L.; Turowski, M.; Cooks, R. G. Rapid Commun. Mass Spectrom. 2001; 15: 2290. DOI: 10.1002/rcm.489
34. Mackay, D.; Shiu, W. Y.; Ma, K. C. *Illustrated Handbook of Physicical-Chemical Properties and Environmental Fate for Organic Chemicals*. CRC Press: Boca Raton, 1992.
35. Pirbazari, M., Borow, H. S., Craig, S., Ravindran, V., McGuire, M. J., Physical Chemical Characterization of Five Earthy-Musty-Smelling Compounds, Wat. Sci. Tech., 1992; 25, 81.

We claim:

1. A combination for identifying and quantifying volatile compounds and semi-volatile compounds in a liquid sample, comprising:
    a hollow core membrane having an inner wall, an outer wall and a lumen;
    a heat element housed within the lumen for establishing a thermal gradient across the membrane that is opposite to a sample concentration gradient across the membrane;
    a sampling pump for pulling the liquid sample over the membrane surface, thereby actively cooling one side of the membrane and enhancing the thermal gradient across the membrane;
    a power source in electrical communication with the heat element; and
    a mass spectrometer for identifying and quantifying analyte in the sample.
2. The combination of claim 1 wherein the heat element is a resistive wire.
3. The combination of claim 2 wherein the wire is a nichrome wire.
4. The combination of claim 1 wherein the power source is a pulsed direct current power supply.
5. The combination of claim 1 wherein the power source is a direct current power supply.
6. The combination of claim 5 wherein the power supply is adjustable.
7. The combination of claim 5 wherein the heat element is a 34 gauge nichrome wire.
8. A method for preparing a sample for on-line identification and quantification of analyte, comprising:
    collecting the sample;
    introducing the-sample directly to a semi-permeable membrane housed in the combination of claim 1;
    establishing a temperature gradient across the membrane that is counter to a concentration gradient; and
    desorbing the analyte from the-membrane into a stream of inert gas, thereby preparing a sample.
9. The combination of claim 1 where the mass spectrometer is a tandem mass spectrometer.
10. The combination of claim 1 where the mass spectrometer is a selected ion monitoring mass spectrometer.
11. The combination of claim 1 having an analyte detection limit of 1 part per million or less for volatile and semi-volatile compounds.
12. The combination of claim 1 having a measurement response time of less than 10 minutes.
13. A method for identifying and quantifying analyte in a liquid sample using membrane introduction mass spectrometry, comprising:

flowing a liquid sample to a membrane, thereby creating a sample concentration gradient across the membrane and actively cooling one side of the membrane;

establishing a thermal gradient that is opposite to the concentration gradient across the membrane;

desorbing the analyte from the membrane and into a stream of an inert gas; and introducing the analyte in the stream of the inert gas into the mass spectrometer, thereby identifying and quantifying the analyte.

14. The method of claim 13 wherein the analyte comprises volatile compounds, semi-volatile compounds or both volatile and semi-volatile compounds.

15. The method of claim 13 wherein flowing a liquid sample to the membrane comprises pulsed sample introduction.

16. The method of claim 13 wherein flowing a liquid sample to the membrane comprises continuous, direct sample introduction.

17. The method of claim 16 wherein the sample is an aqueous sample.

18. The method of claim 17 wherein the aqueous sample is a water sample.

19. The method of claim 13 wherein desorbing the analyte comprises continuous thermally assisted desorption.

20. The method of claim 13 wherein desorbing the analyte comprises pulsed desorption.

21. The method of claim 13 wherein the inert gas is helium.

22. A method for identification and quantification of analyte in a sample, comprising:

providing a combination comprising a hollow core membrane having an inner wall, an outer wall and a lumen, a heat element housed within the lumen for establishing a pulsed thermal gradient across the membrane, a sampling pump for pulling sample over the membrane surface, a power source in electrical communication with the heat element, and a mass spectrometer;

introducing a fluid sample comprising an analyte directly to the membrane;

differentially heating the membrane to establish the pulsed thermal gradient that is opposite to an analyte concentration gradient across the membrane;

desorbing the analyte from the membrane and into a stream of an inert gas; and introducing the analyte in the stream of the inert gas into the mass spectrometer for analysis, thereby identifying and quantifying the analyte.

23. The method of claim 22 wherein the analyte comprises volatile compounds, semi-volatile compounds or both volatile and semi-volatile compounds.

24. The method of claim 22 wherein the sample is a gaseous sample.

25. The method of claim 24 wherein the gaseous sample is an air sample.

26. A method for identification and quantification of analyte in a sample, comprising:

providing a combination comprising a hollow core membrane having an inner wall, an outer wall and a lumen, a heat element housed within the lumen for establishing a continuous or pulsed thermal gradient across the membrane that is opposite to a sample concentration gradient across the membrane, a sampling pump for pulling a liquid sample over the membrane surface, a power source in electrical communication with the heat element, and a tandem or selected ion monitoring mass spectrometer;

introducing liquid sample directly to the membrane;

differentially heating the membrane to establish the thermal gradient;

pulling the liquid sample across the membrane using the sampling pump, thereby actively cooling one side of the membrane and enhancing the thermal gradient;

desorbing the analyte from the membrane and into a stream of an inert gas; and introducing the analyte in the stream of the inert gas into the mass spectrometer for analysis, thereby identifying and quantifying an analyte.

27. The method of claim 26 wherein-the analyte comprises volatile compounds, semi-volatile compounds or both volatile and semi-volatile organic compounds.

28. A combination for analyzing and quantifying an analyte in a flowing sample, comprising:

a hollow core membrane having an inner wall, an outer wall and a lumen;

a heat element housed within the lumen for establishing a pulsed thermal gradient across the membrane that is opposite to a sample concentration gradient across the membrane;

a sampling pump for pulling a fluid sample over the membrane surface;

a power source in electrical communication with the heat element; and a mass spectrometer for analyzing and quantifying an analyte.

29. The combination according to claim 28 where the fluid is a liquid.

30. The combination according to claim 28 where the mass spectrometer is a tandem mass spectrometer.

31. The combination according to claim 28 where the mass spectrometer is a selected ion monitoring mass spectrometer.

32. A combination for monitoring volatile compounds and semi-volatile compounds in a flowing fluid sample, the combination having an analyte detection limit of 1 part per million or less for volatile and semi-volatile compounds and a measurement response times of less than 10 minutes, comprising:

a hollow core membrane having an inner wall, an outer wall and a lumen;

a resistive wire heat element housed within the lumen for establishing a continuous or pulsed thermal gradient across the membrane that is opposite to a sample concentration gradient across the membrane, the heat element being electrically coupled to an adjustable direct current power source or a pulsed direct current power source;

a sampling pump for pulling the fluid sample over the membrane to create a sample concentration gradient across the membrane opposite to the thermal gradient;

an inert gas source for providing an inert gas to receive analyte desorbed from the membrane; and a tandem or selected ion monitoring mass spectrometer for receiving and analyzing analyte desorbed into the inert gas.

* * * * *